US 7,262,195 B2

(12) United States Patent
Li et al.

(10) Patent No.: US 7,262,195 B2
(45) Date of Patent: Aug. 28, 2007

(54) COMPOUNDS USEFUL AS MOTILIN AGONISTS AND METHOD

(75) Inventors: James J. Li, Pennington, NJ (US); Hannguang J. Chao, Lawrenceville, NJ (US); Joseph A. Tino, Lawrenceville, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 403 days.

(21) Appl. No.: 10/940,240

(22) Filed: Sep. 14, 2004

(65) Prior Publication Data

US 2005/0080116 A1   Apr. 14, 2005

Related U.S. Application Data

(60) Provisional application No. 60/503,624, filed on Sep. 17, 2003.

(51) Int. Cl.
*A61K 31/50* (2006.01)
*C07D 237/00* (2006.01)
*C07D 487/00* (2006.01)

(52) U.S. Cl. .................. 514/252.06; 544/230; 544/236

(58) Field of Classification Search ........... 514/252.06; 544/230, 236
See application file for complete search history.

(56) References Cited

U.S. PATENT DOCUMENTS

| | | | |
|---|---|---|---|
| 6,117,896 A | 9/2000 | Qabar et al. | |
| 6,365,592 B1 * | 4/2002 | Leblanc et al. | ........ 514/255.01 |
| 6,858,577 B1 * | 2/2005 | Zhang et al. | ................... 514/2 |

OTHER PUBLICATIONS

Wong et al., "Antigen-antibody Interactions: Elucidation of the Epitope and Strain-Specificity of a Monoclonal Antibody Directed Against the Pilin Protein Adherence Binding Domain of *Pseudomonas aeruginosa* Strain K." Protein Science, vol. 1, No. 10, pp. 1308-1318 (1992).
Bodanszky, M. et al., The Practice of Peptide Synthesis, Second, Revised Edition, Springer-Verlag, publ., pp. ix-xviii (table of contents) (1994).
Brown, J.C. et al., "Motilin, a Gastric Motor Activity Stimulating Polypeptide: The Complete Amino Acid Sequence", Can. J. Biochem., vol. 51, pp. 533-537 (1973).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Greene, T.W. et al., Protective Groups in Organic Synthesis, Third Edition, John Wiley & Sons, Inc., publ., pp. xi-xii (table of contents) (1999).

Janssens, J. et al., "Improvement of Gastric Emptying in Diabetic Gastroparesis by Erythromycin", The New England Journal of Medicine, vol. 322, pp. 1028-1031 (1990).
Peeters, T. et al., "Erythromycin is a motilin receptor agonist", Am. J. Physiol.: Gastrointest. Liver Physiol., vol. 257, No. 3, Pt. 1, pp. G470-G474 (1989).
Thielemans, L. et al., "The motilin pharmacophore in CHO cells expressing the human motilin receptor", Biochemical and Biophysical Research Communications, vol. 293, pp. 1223-1227 (2002).
Van Assche, G. et al., "Contractile effects and intracellular $Ca^{2+}$ signalling induced by motilin and erythromycin in the circular smooth muscle of human colon", Neurogastroenterology and Motility, vol. 13, No. 1, pp. 27-35 (2001).
Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

* cited by examiner

*Primary Examiner*—Kamal A. Saeed
*Assistant Examiner*—Susannah L. Chung
(74) *Attorney, Agent, or Firm*—Burton Rodney

(57) ABSTRACT

Compounds are provided which are useful in treating disorders of gastrointestinal motility and which have the structure $$Q\underset{H}{\overset{O}{\underset{\|}{N}}}\underset{H}{\overset{R_1}{\underset{*}{C}}}\underset{O}{\overset{H}{\underset{\|}{N}}}\underset{Z}{\overset{R_2}{\underset{*}{C}}}$$

or a pharmaceutically acceptable salt thereof, a prodrug ester thereof, and all stereoisomers thereof,
wherein $R_1$ and $R_2$ are the same or different and are independently selected from hydrogen, alkyl, aryl, cycloalkyl, alkenyl, alkynyl, arylalkyl, heteroaryl, heteroarylalkyl or heterocycloalkyl;
Z is selected from $-CON(R_4)R_{4a}$, $-CO_2R_4$, $-SO_2N(R_4)R_{4a}$, $-SO_2R_4$, CN, and

[structures of five heterocyclic rings shown: tetrazole, imidazole-$R_{4b}$, pyrazole-$R_{4b}$, oxazole-$R_{4b}$, isoxazole-$R_{4b}$]

$R_4$ and $R_{4a}$ are the same or different and are independently selected from hydrogen, alkyl, cycloalkyl, aryl, arylalkyl, heteroaryl, or heteroarylalkyl or $R_4$ and $R_{4a}$ can be joined together to form a heterocycle.
$R_{4b}$ is selected from hydrogen, halogen, hydroxyl, CN, $OCF_3$, $CF_3$, $CONH_2$, $SONH_2$, $SO_2CH_3$, $NHCOCH_3$ or $NHCO_2CH_3$; and
Q is a substituted bicyclic heterocycle.

A method for using such compounds for treating disorders of gastrointestinal motility is also provided.

7 Claims, No Drawings

COMPOUNDS USEFUL AS MOTILIN AGONISTS AND METHOD

FIELD OF THE INVENTION

This application claims a benefit of priority from U.S. Provisional Application No. 60/503,624 filed Sep. 17, 2003, the entire disclosure of which is herein incorporated by reference.

The present invention relates to novel compounds which are motilin agonists and to a method for using such compounds for the treatment of gastrointestinal motility disorders.

BACKGROUND OF THE INVENTION

Gastrointestinal motility regulates the orderly movement of ingested material through the gut to insure adequate absorption of nutrients, electrolytes and fluids. Appropriate transit through the esophagus, stomach, small intestine and colon depends on regional control of intraluminal pressure and several sphincters that regulate forward movement and prevent back-flow of gastrointestinal contents. The normal gastrointestinal motility pattern may be impaired by disease, surgery or by adverse reaction to drug treatment for non-gastrointestinal disease.

Motilin is a 22 amino acid peptide that is secreted from enterochromaffin cells in the small intestine into the bloodstream, binds to a G-protein coupled receptor, GPR38, and is involved in the normal regulation of coordinated motility of the gastrointestinal tract (J. C. Brown, M. A. Cook, J. R. Dryburgh; *Can. J. Biochem.*, 1973, 51:533). There is also evidence that the motilin receptor is expressed in the colon and motilin has been shown to increase cell calcium and to stimulate contraction of human colonic smooth muscle (G. Van Assche, I. Depoortere, T. Thijs, L. Missiaen, F. Pennenckx, H. Takashi, K. Geboes, J. Janssens, and T. L. Peeters, *Neurogastroentero. Mot.* 2001, 13:27-35). Erythromycin is a motilin agonist and is used therapeutically to increase the rate of gastric emptying (T. Peeters, G. Matthijs, I. Depoortere, T. Cachet, J. Hoogmartens, G. Vantrappen, *Am. J. Physiol. Gastrointest Liver Physiol.,* 1989, 257, G470-G474; J. Janssens, T. L. Peeters, G. Vantrappen, J. Tack, J. L. Urbain, M. DeRoo, E. Muls, R. Bouillon, *N. Engl. J. Med.* 1990, 322, 1028-1031). In addition, motilin peptide analogs and motilides have been shown to stimulate contraction in antral and colonic gastrointestinal muscle strips (L. Thielemans, I. Depoortere, J. V. Broeck, and T. L. Peeters, *Biochem. Biophys. Res. Comm.* 2002, 293, 1223-1227). Therefore, it is expected that potent motilin agonists will act as a prokinetic agent and be useful for the treatment of delayed gastric emptying (gastroparesis) in normal and diabetic patients, postoperational ileus, irritable bowel syndrome, functional dyspepsia, chronic constipation, gastroesophogeal reflux disease or other conditions where motility is delayed. It will also be useful for treatment of colonic motility disorders including colonic hypomotility. Moreover, motilin agonists will promote gastrointestinal motility in a coordinated manner, thereby avoiding some common side effects associated with other prokinetic agents, such as nausea, constipation, and diarrhea.

Other examples of disorders whose symptoms include impaired gastrointestinal motility are anorexia, gall bladder stasis, postoperative paralytic ileus, scleroderma, intestinal pseudoobstruction, gastritis, emesis, and chronic constipation (colonic inertia). These gastrointestinal disorders are generally treated with prokinetic agents that enhance propulsive motility and thus could be treated with a motilin agonist.

U.S. Pat. No. 6,117,896 to Qabar et al. discloses β-sheet mimetics which have the structure

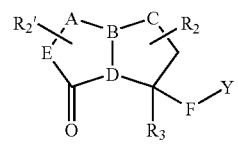

wherein

A is selected from $-(=O)-$, $-(CH_2)_{0-4}-$, $-C(=O)(CH_2)_{1-3}-$, $-(CH_2)_{1-20}-$ and $-(CH_2)_{1-2}S-$;

B is selected from N and CH;

C is selected from $-C(=O)-$, $-(=O)(CH_2)_{1-3}-$, $-(CH_2)_{0-3}-$, $-O-$, $-S-$, $-O-(CH_2)_{1-2}-$ and $-S(CH_2)_{1-2}-$;

D is selected from N and $C(R_4)$;

E is selected from

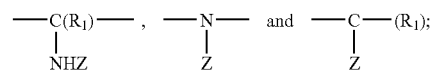

F is an optional carbonyl moiety;

$R_1$ and $R_4$ are independently selected from amino acid side chain moieties and derivatives thereof;

$R_2$ and $R_2'$ represent one or more ring substituents individually selected from an amino acid side chain moiety and derivatives thereof, or $R_2$ taken together with C or Y forms a fused substituted or unsubstituted homocyclic or heterocyclic ring;

$R_3$ is selected from an amino acid side chain moiety and derivatives thereof, or taken together with C forms a bridging moiety selected from $-(CH_2)_{1-2}-$, $-O-$ and $-S-$;

Y and Z represent the remainder of the molecule; and any two adjacent CH groups of the bicyclic ring may form a double bond.

In one embodiment, $R_2$ taken together with C forms a heterocyclic fused ring as represented by

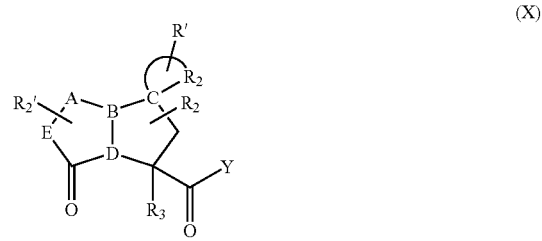

(X)

wherein A, B, C, D, E, $R_2$, $R_2'$, $R_3$ and Y are as defined above, and R' is one or more optional ring substituents.

In one aspect of structure (X), $R_2$ and C taken together form a fused five-, six-, seven- or eight-membered ring as represented by structure (Xb):

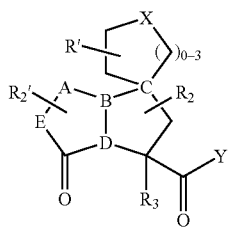

(Xb)

wherein A, B, C, D, E, Y, $R_2$, $R_2'$, $R_3$ and R' are as defined above, and X is selected from —C(=O)—, —NH—, —NR'—, —O— and —S—.

SUMMARY OF THE INVENTION

In accordance with the present invention, novel compounds are provided which are motilin agonists and have the general structure of formula I:

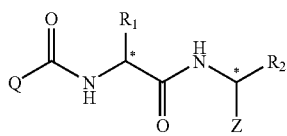

I wherein $R_1$ and $R_2$ are the same or different and are independently selected from hydrogen, alkyl, aryl, cycloalkyl, alkenyl, alkynyl, arylalkyl, heteroaryl, heteroarylalkyl or heterocycloalkyl;

Z is selected from —CON($R_4$)$R_{4a}$, —CO$_2$$R_4$, —SO$_2$N($R_4$)$R_{4a}$, —SO$_2$$R_4$, CN, and

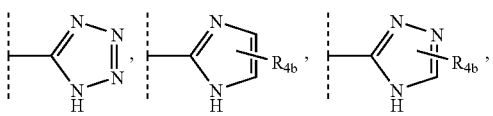

$R_4$ and $R_{4a}$ are the same or different and are independently selected from hydrogen, alkyl, cycloalkyl, aryl, arylalkyl, heteroaryl, heteroarylalkyl or $R_4$ and $R_{4a}$ can be joined together to form a heterocycle;

$R_{4b}$ is selected from hydrogen, halogen, hydroxyl, CN, OCF$_3$, CF$_3$, CONH$_2$, SONH$_2$, SO$_2$CH$_3$, NHCOCH$_3$ or NHCO$_2$CH$_3$;

Q is selected from the following substituted bicyclic heterocycles.

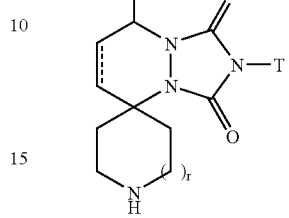

wherein r is 0, 1 or 2;

represents a single bond or a double bond; and

T is selected from alkyl, aryl, cycloalkyl, alkenyl, alkynyl, arylalkyl, heteroaryl, heteroarylalkyl and heterocycloalkyl, and where each of these groups may be optionally substituted with $R_5$, $R_{5a}$ and $R_{5b}$;

$R_5$, $R_{5a}$ and $R_{5b}$ are the same or different and are independently selected from hydrogen, halogen, hydroxyl, OCF$_3$, CF$_3$, CN, NR$_{5c}$(R$_{5d}$), C(O)NR$_5$C(R$_{5d}$), OC(O)NR$_{5c}$(R$_{5d}$), OR$_{5c}$, SO$_2$R$_{5c}$, SO$_2$N(R$_{5c}$)R$_{5d}$, alkyl, alkoxyl, aryl, arylalkyl, heteroaryl, heteroarylalkyl or heterocycloalkyl. Further, $R_5$ and $R_{5a}$ can be joined together with —OCH$_2$O— or —OCH$_2$CH$_2$O— to form a fused bicyclic ring with aryl or a heteroaryl group;

$R_{5c}$ and $R_{5d}$ are the same or different and are independently selected from hydrogen, alkyl, cycloalkyl, aryl, arylalkyl, heteroaryl, heteroarylalkyl, heterocycloalkyl or $R_{5c}$ and $R_{5d}$ can be joined together to form a heterocycle.

Preferred are compounds with formula I wherein Z is selected from —CON($R_4$)$R_{4a}$, —CO$_2$$R_4$, —SO$_2$N($R_4$)$R_{4a}$ and —SO$_2$$R_4$; and $R_1$, $R_2$, $R_4$, $R_{4a}$, Q, are defined as above; and r is an integer from 0, 1 or 2, preferably 1.

Most preferred are compounds with formula I wherein Z is CONH$_2$ and Q is

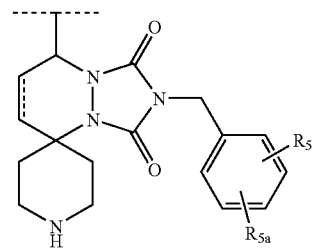

$R_1$, $R_2$, $R_5$ and $R_{5a}$ are defined as above.

Examples of preferred compounds of the invention include the following:

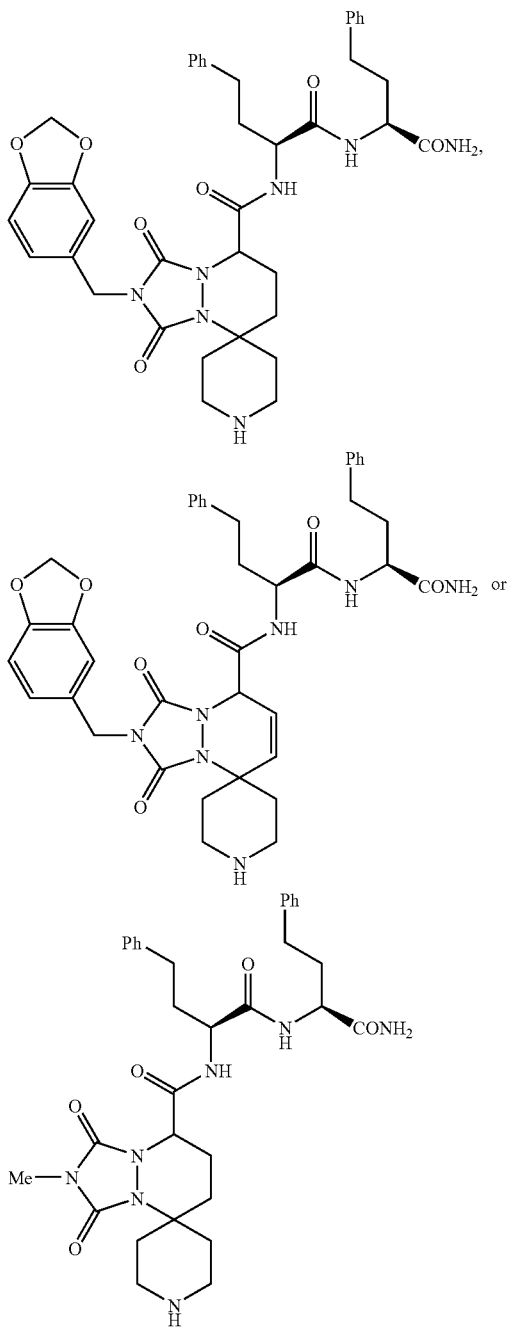

In addition, in accordance with the present invention, a method is provided for treating patients suffering from impaired gastrointestinal motility or disorders involving gastrointestinal motility or for increasing levels of endogenous growth hormone which includes the step of administering to a human patient, dog or cat in need thereof a therapeutically effective amount of a compound of the present invention. Illustrative examples of disorders that may be treated with the inventive compounds include but are not limited to gastroparesis, gastroesophageal reflux disease, anorexia, gall bladder stasis, postoperative paralytic ileus, scleroderma, intestinal pseudoobstruction, gastritis, emesis, chronic constipation (colonic inertia), irritable bowel syndrome, functional dyspepsia, or other conditions where motility is delayed as well as colonic motility disorders including colonic hypomotility or muscular functional decline with age where endogenous growth hormone is involved.

DETAILED DESCRIPTION OF THE INVENTION

The following abbreviations are employed herein:
Boc=tert-butoxycarbonyl
Boc$_2$O=di-tert-butyldicarbonate
Cbz=benzyloxycarbonyl (or carbobenzoxy)
Conc. HCl=concentrated aqueous hydrochloride
DIEA or DIPEA=diisopropylethylamine
DMAP=4-(dimethylamino)pyridine
DMF=N,N-dimethylformamide
EDAC=1-(3-dimethylaminopropyl)-3-ethylcarbodiimide hydrochloride
EtOAc=ethyl acetate
HOAT or HOAt=1-hydroxy-7-azabenzotriazole
HOBT=1-hydroxybenztriazole
HPLC or LC=high performance liquid chromatography
LC/MS=high performance liquid chromatography/mass spectrometry
MS or Mass Spec=mass spectrometry
NaOH=sodium hydroxide
Na$_2$SO$_4$=sodium sulfate
Pd/C=palladium on activated charcoal
PyAOP=7-(azabenzotriazole-1-yloxy)tripyrrolidino-phosphonium hexafluorophosphate
TFA=trifluoroacetic acid
THF=tetrahydrofuran
YMC=trademark of YMC Co, Ltd., Kyoto, Japan
g=gram(s)
h or hr=hour(s)
min=minute(s)
ml=milliliter
mg=milligram(s)
mol=moles
mmol=millimole(s)
nM=nanomolar
RT=room temperature
Rt=HPLC or LC retention time
Et=ethyl
i-Pr=isopropyl
Me=methyl.

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one to three functional groups (which may be the same or different) commonly attached to such chains, such as, but not limited to alkyl, aryl, alkenyl, alkynyl, hydroxy, arylalkyl, cycloalkyl, cycloalkylalkyl, alkoxy, arylalkyloxy, alkanoyl, amino, halo, thio, cyano, carboxyl, carbonyl

, amino, aminocarbonyl, alkoxylcarbonyl, amido, haloaryl, $CF_3$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 12 carbons, forming the ring, and which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

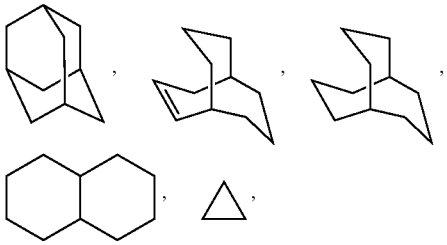

any of which groups may be optionally substituted with 1 to 3 substituents as defined above for alkyl.

Unless otherwise indicated, the term "aryl", as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

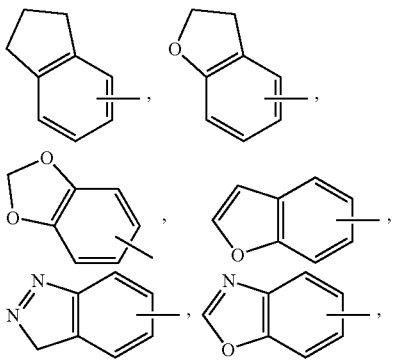

and may be optionally substituted through available carbon atoms with 1, 2, or 3 groups selected from hydrogen, halo, alkyl, alkoxy, alkenyl, trifluoromethyl, trifluoromethoxy, alkynyl, cycloalkyl, heterocyclicalkyl, aryl, heteroaryl, arylalkyl, aryloxy, aryloxyalkyl, arylalkoxy, and/or any of the substituents for alkyl set out herein.

The term "arylalkyl" as used herein alone or as part of another group refers to alkyl groups as defined above having an aryl substituent, such as benzyl, phenethyl or naphthylpropyl, wherein said aryl and/or alkyl groups may optionally be substituted as defined above.

The term "alkoxy" or "aryloxy" as employed herein alone or as part of another group includes an alkyl or aryl group as defined above linked through an oxygen atom.

Unless otherwise indicated, the term "alkenyl" as used herein by itself or as part of another group refers to straight or branched chain radicals of 2 to 20 carbons, preferably 3 to 12 carbons, and more preferably 2 to 6 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with one or more functional groups as defined above for alkyl.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

Unless otherwise indicated, the term "acyl" as employed herein by itself or part of another group, as defined herein, refers to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "heterocycloalkyl" or "cycloheteroalkyl" as used herein alone or as part of another group refers to a 4-, 5-, 6- or 7-membered saturated or partially unsaturated ring which includes 1 to 3 hetero atoms such as nitrogen, oxygen and/or sulfur, linked through a carbon atom or a heteroatom, such as

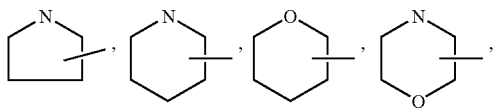

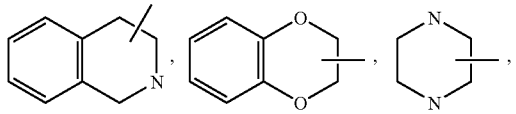

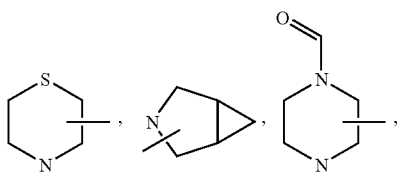

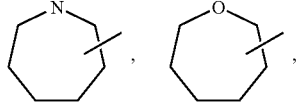

and the like. The above groups may include 1 to 4 substituents such as alkyl, halo, oxo and/or any of of the substituents for alkyl or aryl set out herein. In addition, any of the heterocycloalkyl rings can be fused to a cycloalkyl, aryl, heteroaryl or heterocycloalkyl ring.

Unless otherwise indicated, the term "heteroaryl" as used herein alone or as part of another group refers to a 5-, 6- or 7-membered aromatic ring which includes 1, 2, 3 or 4 hetero atoms such as nitrogen, oxygen or sulfur, SO or SO₂, and such rings fused to an aryl, cycloalkyl, heteroaryl or cycloheteroalkyl ring (e.g. benzothiophenyl, indolyl), and includes possible N-oxides, linked through a carbon atom or a heteroatom. The heteroaryl group may optionally include 1 to 4 substituents such as any of the substituents for alkyl or aryl set out above. Examples of heteroaryl groups include the following:

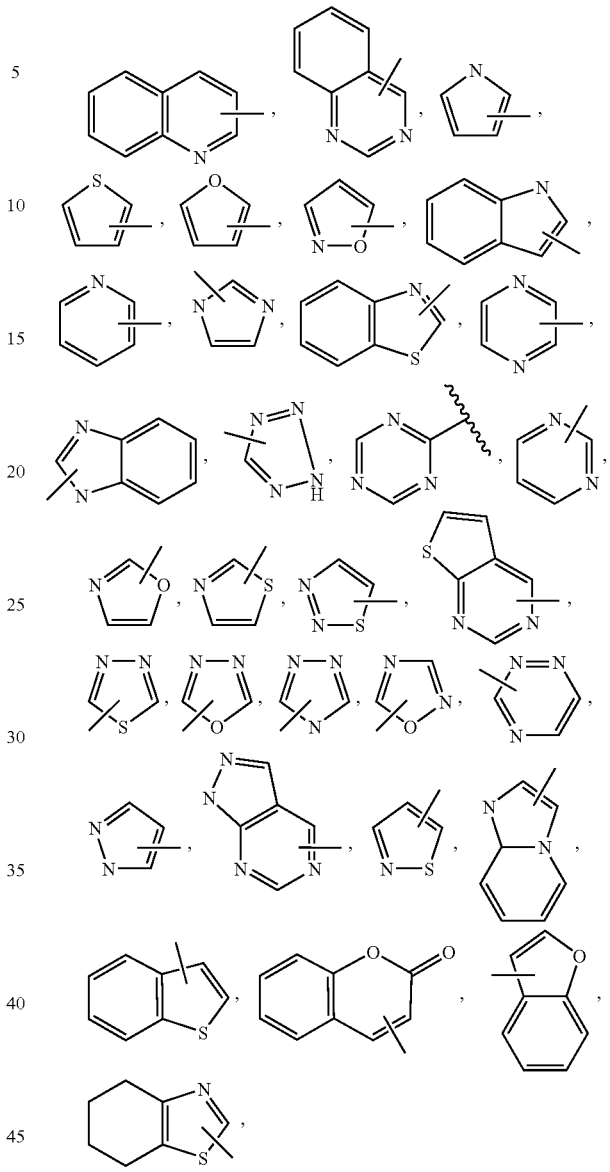

and the like.

The term "heteroarylalkyl" as used herein alone or as part of another group refers to a heteroaryl linked through an alkyl group.

The term "heterocyclo", "heterocycle" or "heterocyclic", as used herein, represents an unsubstituted or substituted stable 4-, 5-, 6- or 7-membered monocyclic ring system which may be saturated or unsaturated, and which consists of carbon atoms and from one to four heteroatoms selected from N, O, S and or a SO or SO₂ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl and oxadiazolyl, as well as any of the heteroaryl groups and cycloheteroalkyl groups set out above.

Optionally a heterocyclo group may be substituted with one or more functional groups, such as those described for alkyl.

The term "alkoxyalkyl" or "aryloxyalkyl" as used herein alone or as part of another group refers to a alkoxy or aryloxy group respectively, linked through an alkyl group.

Any compound that can be converted in vivo to provide the bioactive agent (i.e., the compound of formula I) is a prodrug within the scope and spirit of the invention.

Various forms of prodrugs are well known in the art and are described in:

*The Practice of Medicinal Chemistry*, Camille G. Wermuth et al., Ch 31, (Academic Press, 1996);

*Design of Prodrugs*, edited by H. Bundgaard, (Elsevier, 1985); and

*A Textbook of Drug Design and Development*, P. Krogsgaard-Larson and H. Bundgaard, eds. Ch 5, pgs 113-191 (Harwood Academic Publishers, 1991).

The compounds of the present invention all have at least two asymmetric centers as noted by the asterisks in formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. One isomer might be slightly preferred in some cases, but both are claimed. The racemic mixtures may be separated into individual optical isomers employing conventional procedures such as by chromatography or fractional crystallization.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

General Synthetic Schemes

The compounds of the present invention may be prepared according to the following general synthetic reaction schemes as well as relevant published literature procedures that may be used by one skilled in the art. Exemplary reagents, procedures and conditions for these reactions appear hereinafter and in the working examples. Starting materials are commercially available or can be readily prepared by one of ordinary skill in the art using known methods. Unless otherwise specified the various substituents of the compounds are defined in the same manner as the formula I compounds. During the preparation of compounds of formula I, one or more protecting groups might be used, reaction conditions for protection and deprotection may be found in the "Protective Groups in Organic Synthesis" Greene et al., John Wiley and Sons Inc, 1999, or other methods used by one of ordinary skill in the art.

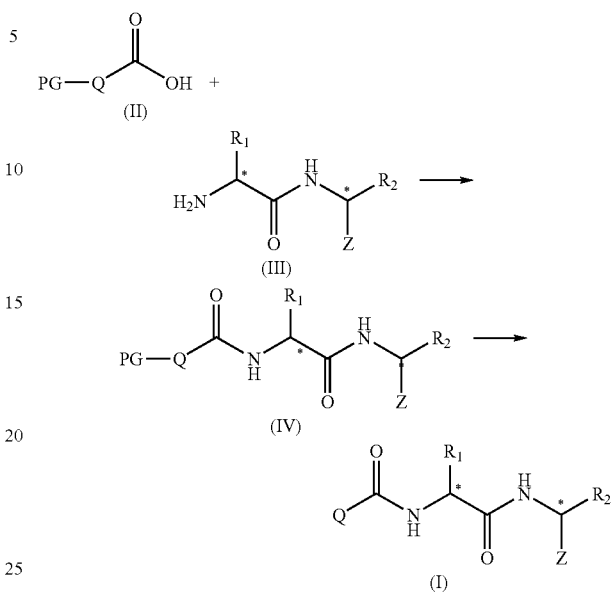

Scheme I

Scheme I describes a general synthetic sequence for the preparation of the compounds of formula I of the invention. Compounds of formula IV can be prepared from carboxylic acids II and amines III using an appropriate carboxylic acid activating reagent in an inert solvent. The above reaction is carried out employing a molar ratio of II:III within the range from about 3:1 to about 0.3:1, preferably from about 1.2:1 to about 0.8:1, at a temperature within the range from about −20 to about 50° C., preferably from about 20 to about 30° C. Exemplary carboxylic acid activating agents include isobutylchloroformate, carbonyldiimidazole, dicyclohexylcarbodiimide, pentafluorophenol trifluoroacetate, 7-(azabenzotriazole-1-yloxy)tripyrrolidino-phosphonium hexafluorophosphate or 1-(3-dimethylaminopropyl)-3-ethylcarbodiimide. Exemplary inert solvents include methylene chloride, tetrahydrofuran, N,N-dimethylformamide, ethers, dioxane, or acetonitrile. The above reaction can also be carried by other methods described in Bodanszky, M. and Bodanszky, A. *The Practice of Peptide Synthesis* 1994, Springer-Verlag Berlin Heidelberg, New York, N.Y.

In some cases, there is an amine-protecting group (PG), such as Boc, CBZ or Trityl in the Q moiety of compound IV. The protecting group may be removed to afford the final compounds of formula I. Exemplary deprotection reagents for Boc are hydrogen chloride in dioxane or TFA in dichloromethane. Exemplary deprotection for CBZ is catalytic hydrogenation or trimethylsilyl iodide in methylene chloride. Exemplary deprotection for Trityl is hydrogen chloride in acetone or tetrahydrofuran. Additional conditions for deprotection may be founds in the "Protective Groups in Organic Synthesis" Greene et al., John Wiley and Sons Inc, 1999, or other methods used by one of ordinary skill in the art. Amines III including peptide amides or peptide mimics can be prepared by methods used by one of ordinary skill in the art.

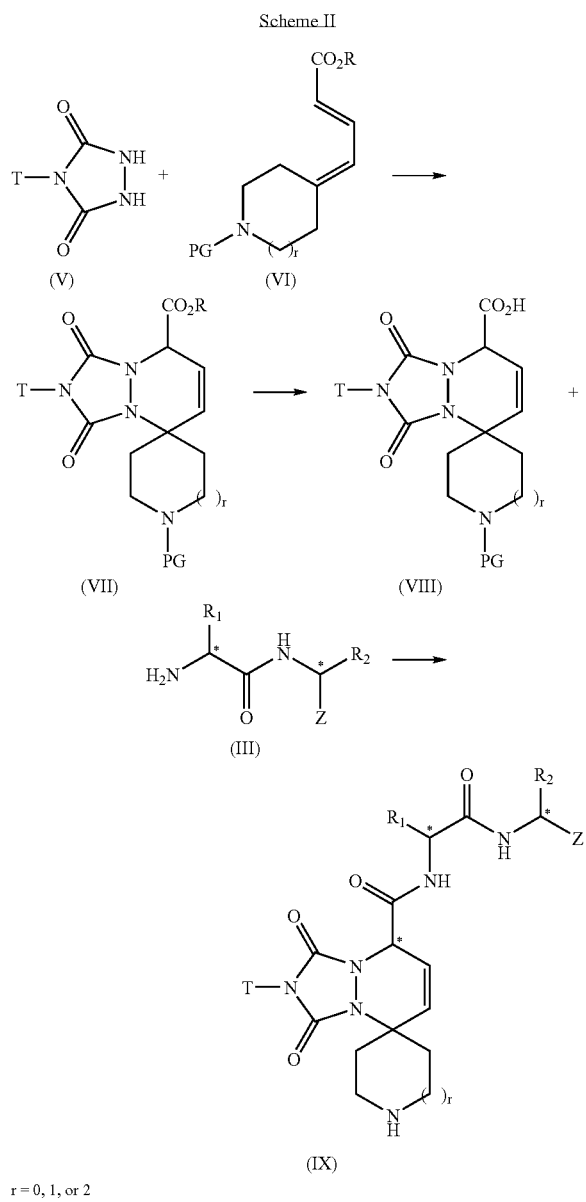

Scheme II r = 0, 1, or 2

Scheme II describes a general synthetic sequence for the preparation of the compounds of formula IX, a set of preferred compounds I. Compounds of formula VII can be prepared from a triazolidinedione V and pentadienoic ester VI in a two-step sequence. Treatment of triazolidinedione V with an oxidant such as bis(triacetoxy)iodobenzene or bis(trifluoroacetoxy)iodobenzene gives triazoledione in situ, which is then allowed to react with pentadienoic ester VI via a [4+2] cycloaddition to give compounds of formula VII. The above reaction is carried out employing a molar ratio of V:VI within the range from about 5:1 to about 1:1, preferably from about 1.5:1 to about 1:1, at a temperature within the range from about −20 to about 50° C., preferably from about 0 to about 25° C.

Basic hydrolysis of compounds VII using aqueous sodium hydroxide or lithium hydroxide provides unsaturated compounds of formula VIII.

Hydrogenation of compounds VII followed by basic hydrolysis also provides saturated compounds of formula VIII.

Alternatively, hydrogenation can be accomplished after the basic hydrolysis to give saturated compounds of formula VIII. Compound IX can be prepared from compounds VIII and amines III in a similar manner according to the conditions described in Scheme I.

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

The compounds of the present invention may be employed in combination with other motilin agonists or other suitable therapeutic agents useful in the treatment of the aforementioned disorders including agents to treat gastrointestinal disorders such as proton pump inhibitors, for example, esomeprazole, lansoprazole or omeprazole; histamine H2 receptor blockers, for example, nizatidine, famotidine, cimetidine, or ranitidine; antiacid agents such as aluminum antacids, calcium antacids, and magnesium antacids, and combinations as listed in the Physicians' Desk Reference (PDR); gastrointestinal stimulants, for example, metoclopramide; dopamine receptor blockers, for example, domperidone, fenoldapam mesylate, cabergoline, pramipexole, pergolide mesylate, ropinirole and amanitidine HCl; 5-HT4 agonists, for example, tegaserod (Zelnorm®) and 5-HT3 antagonists, for example, alosetron, as well as agents for treating anorexia, gall bladder stasis, agents for treating postoperative paralytic ileus, agents for treating scleroderma, agents for treating intestinal pseudo-obstruction, anti-gastritis agents, anti-emesis agents, anti-constipation agents, agents for treating irritable bowel syndrome, agents for treating functional dyspepsia, and agents for treating colonic hypomotility. The listing of the above agents include those agents disclosed in the PDR.

The above other therapeutic agents, when employed in combination with the compounds of the present invention, may be used, for example, in those amounts indicated in the PDR or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxymethyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal, aerosol, or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 0.001 to 100 mg/kg of body weight of active compound per day, preferably 0.01 to 1 mg/kg of body weight of active compound per day, that can be administered in a single dose or in the form of individual divided doses, such as from 1 to 4 times per day. In general, treatment regimens according to the present invention comprise administration to a human subject in need of such treatment of from about 5 mg to about 1000 mg of the compound(s) of the present invention per day in single or multiple doses. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to motility-associated conditions.

The following examples serve to better illustrate, but not limit, preferred embodiments of the invention.

EXAMPLES

General Experimental

The following examples represent preferred embodiments of the invention. All temperatures are in ° C. unless indicated otherwise.

The term LC refers to a Shimadzu high performance liquid chromatography using a 4 minute gradient of 0-100% solvent B [MeOH:H$_2$O:0.2% H$_3$PO$_4$] with a 1 min. hold, an ultra violet (uv) detector set at 220 nM and using a column (4.6×50 mm) packed with YMC C18 5 micron resin.

The term preparative LC refers to an automated Shimadzu system using the YMC ODS C18 5 micron preparative columns, and mixtures of solvent A (10% MeOH/90% H$_2$O/0.2% TFA) and solvent B (90% MeOH/10% H$_{20}$/0.2% TFA).

Example 1

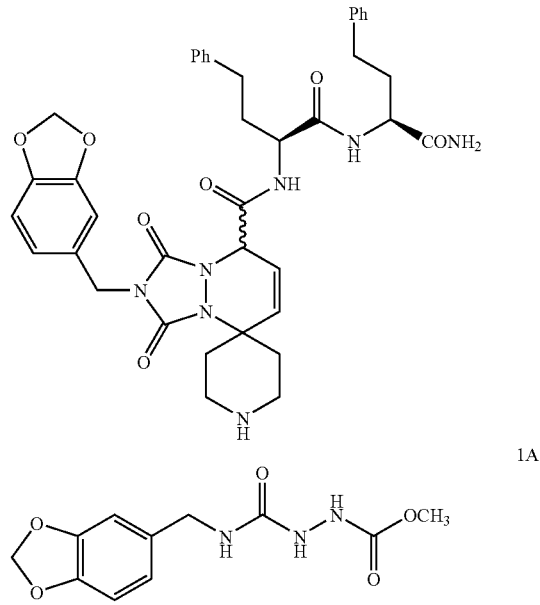

1A

To 50 mL of anhydrous THF were added benzodioxol-5-yl-methylamine (9.1 g, 60.2 mmol) and hydrazinecarboxylic acid methyl ester (5.4 g, 60.0 mmol) followed by addition of carbonyldiimidazole (9.7 g, 60.0 mmol), all at RT. The solution was stirred under N$_2$ overnight. The resulting solid was filtered, washed with anhydrous THF and dried under vacuum to give a white solid 1A (10 g, 62%). LC=68% purity; Rt=2.00 min. LC-MS m/z=268 (M+H).

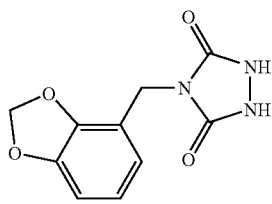

1B

To 40 mL of 4N KOH aqueous solution was added 1A (10 g, ~26 mmol), and stirred at 100° C. for 3 h. After cooling to RT, the solid was filtered off, and aqueous filtrate was acidified with conc. HCl. The resulting precipitate was filtered and dried under vacuum to give a pale-yellow solid 1B (4.1 g, 58%). LC=95% purity; Rt=2.24 min. LC-MS m/z=135 (M-triazolidinedione).

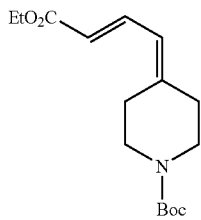

1C

To a stirred solution of 4-(diethoxyphosphoryl)-butenoic acid ethyl ester (6.5 mL, 26.4 mmol) in 50 mL of anhydrous DMF was added sodium hydride (1.17 g, 29.3 mmol, ~60%) at 0° C. The reaction was stirred at RT for 30 min, followed by addition of 4-oxopiperidine-1-carboxylic acid tert-butyl ester (5.2 g, 26.1 mmol), and stirred for another 6 h at RT. The reaction was quenched with water, then diluted with EtOAc. The mixture was washed with water (5×), dried over Na$_2$SO$_4$, filtered and concentrated. Purification by flash chromatography on silica gel (1:9 EtOAc/hexanes as elutant) gave a white solid 1C (6.5 g, 84%). LC=99% purity; Rt=4.31 min. LC-MS m/z=318 (M+Na).

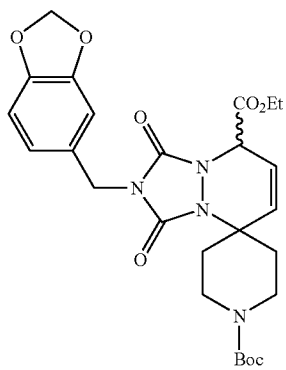

1D

To a stirred solution of 1B (3.32 g, 14.1 mmol) in 35 mL of anhydrous DMF was added bis(trifluoroacetoxy)iodobenzene (6.07 g, 14.1 mmol) at 0° C., and the mixture was stirred at 0° C. for 2 h. A solution of 1C in 35 mL anhydrous acetone was added at 0° C. to the above solution, and the resulting mixture was stirred at RT overnight. The reaction was quenched with water, then diluted with EtOAc. The mixture was washed with water (5×), dried over Na$_2$SO$_4$, filtered and concentrated. Purification by flash chromatography on silica gel (30-50% EtOAc/hexanes as elutant) gave a white foam solid 1D (3.46 g, 46%). LC=98% purity; Rt=4.12 min. LC-MS m/z=551 (M+Na).

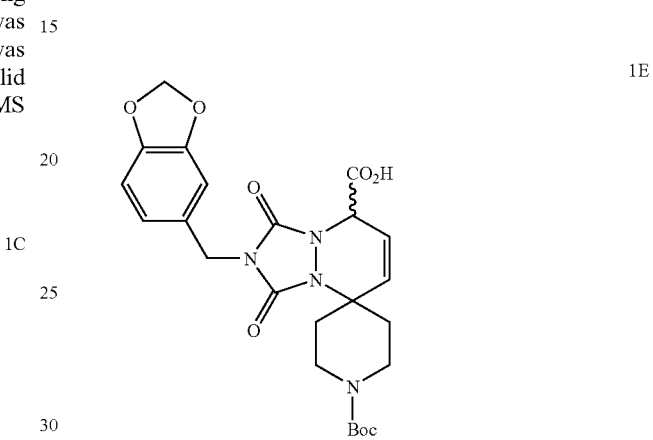

1E

To a stirred solution of 1D (3.46 g, 6.55 mmol) in a mixed solvent of THF (15 mL) and ethanol (7 mL) was added 13 mL of 1N NaOH at RT, and stirred at RT for 2 h. The solution was acidified with 1N HCl, then concentrated. It was extracted with EtOAc (3×), dried over Na$_2$SO$_4$, filtered and concentrated to give a light yellow foam solid 1E (3.4 g, 100%). LC=97% purity; Rt=3.87 min. LC-MS m/z=501 (M+H).

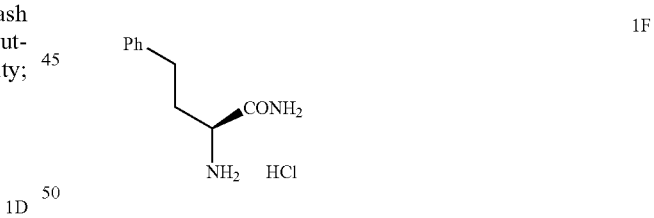

1F

To a stirred solution of 2-tert-butoxycarbonylamino-4-phenylbutyric acid (1.25 g, 4.5 mmol) in 10 mL DMF were added EDAC (1.7 g, 8.9 mmol) and HOAT (1.2 g, 8.8 mmol), and the resulting mixture was stirred at RT for 3 h. An aqueous solution of saturated ammonium hydroxide (5.2 g, 44.5 mmol, ~30%) was added, and the mixture was stirred at RT overnight. The reaction was diluted with EtOAc, washed with water (5×), 1N NaOH (3×), water again, dried over Na$_2$SO$_4$, filtered and concentrated. The resulting solid was dissolved in 5 mL of dichloromethane followed by addition of 10 mL of 20% TFA in dichloromethane, and the mixture was stirred at RT for 2 hr. The compound was concentrated, redissolved in EtOAc, washed with 1N NaOH, water, dried over Na$_2$SO$_4$, filtered and concentrated. The compound was redissolved in diethylether, followed by addition of 0.5 mL of conc. HCl. It was concentrated to give a white foam solid 1F (680 mg, 70%) as HCl salt. LC=85% purity; Rt=0.82 min. LC-MS m/z=179 (M+H).

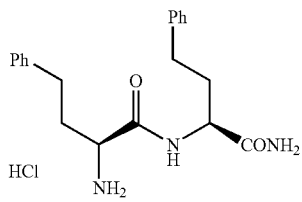

1G

To 2-tert-butoxycarbonylamino-4-phenylbutyric acid (56 mg, 0.2 mmol) in a mixed solvent of DMF (0.2 mL) and dichloroethane (0.8 mL) were added EDAC (42 mg, 0.22 mmol) and HOAT (30 mg, 0.22 mmol) and IF (43 mg, 0.2 mmol) and the mixture was stirred at RT for 16 h. The reaction was diluted with EtOAc, washed with water (2×), dried over Na$_2$SO$_4$, filtered and concentrated. The intermediate was purified on prepLC, then de-Boc with 2 mL of 4N HCl/dioxane solution at RT for 30 min. It was concentrated to give an oil as 1G (45 mg, 60%) as HCl salt. LC=97% purity; Rt=1.79 min.

Example 1

To a stirred solution of 1E (50 mg, 0.1 mmol) in 0.8 mL of DMF were added EDAC (19.2 mg, 0.1 mmol), HOAt (14 mg, 0.1 mmol), DIEA (18 μL, 0.1 mmol) and 1G (34 mg, 0.09 mmol) and the mixture stirred at RT overnight. The reaction was diluted with EtOAc, washed with water (2×), 1N NaOH (2×), water again, dried over Na$_2$SO$_4$, filtered and concentrated. The intermediate was purified on prepLC, then de-Boc with 1 mL of 50% TFA/CH$_2$Cl$_2$ solution at RT for 30 min. It was concentrated to give 31 mg (40%) of the title compound (Example 1) as foamy solid. LC=97% purity, Rt=2.93 min; LC-MS m/z=722 (M+H).

Example 2

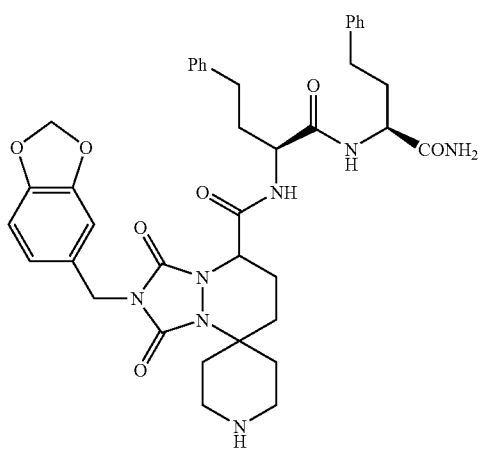

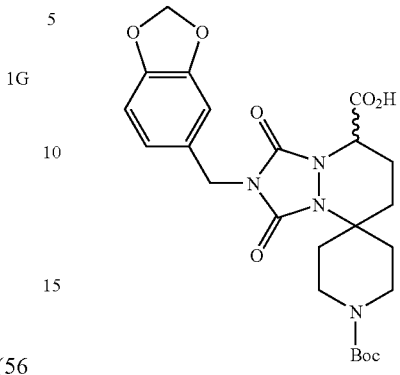

2A

To a stirred solution of the Example 1, Part 1E compound (2.7 g, 5.4 mmol) in 15 mL of methanol was added 270 mg of Pd/C catalyst under N$_2$. The reaction mixture was flushed several times with hydrogen gas, and stirred under a hydrogen gas balloon at RT overnight. The catalyst was filtered off, and filtrate was concentrated to give a white foam solid 2A (2.6 g, 96%). LC=94% purity; Rt=3.67 min. LC-MS m/z=503 (M+H).

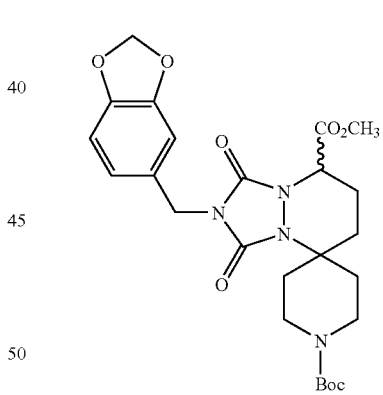

2B

To a stirred solution of 2A (1.7 g, 3.4 mmol) in a mixed solvent of anhydrous toluene (10 mL) and methanol (6 mL) was added an azidotrimethylsilane solution (2.5 mL, 2M in toluene, 5 mmol), and the mixture was stirred at RT overnight. The reaction mixture was concentrated, then diluted with water and EtOAc. The mixture was washed with water (2×), dried over Na$_2$SO$_4$, filtered and concentrated. Purification by flash chromatography on silica gel (30-50% EtOAc/hexanes as elutant) gave a white foam solid 2B (1.7 g, 92%). LC=98% purity; Rt=3.78 min. LC-MS m/z=415 (M-Boc).

21

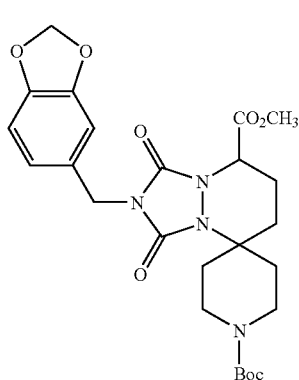

2B-E1 and 2B-E2

Compound 2B (1.7 g) was separated on a chiral preparative HPLC column packed with ChiralPak AS 2 μM (5×50 cm) using 10% absolute ethanol/90% hexanes as the solvents. The first eluting enantiomer was 2B-E1 (700 mg, 99% ee) and the second eluting enantiomer was 2B-E2 (720 mg, 84% ee).

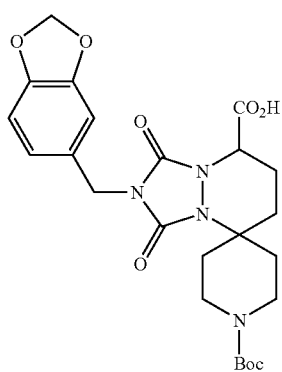

2A-E1

To a stirred solution of 2B-E1 (97 mg, 0.19 mmol) in 1 mL of methanol was added 0.38 mL of 1N NaOH at RT, and stirred at RT for 2 h. The solution was acidified with 1N HCl, then concentrated. It was extracted with EtOAc (3×), dried over Na$_2$SO$_4$, filtered and concentrated to give a white foam solid 2A-E1 (88 mg, 94%). LC=98% purity; Rt=3.63 min. LC-MS m/z=503 (M+H).

22

Example 2

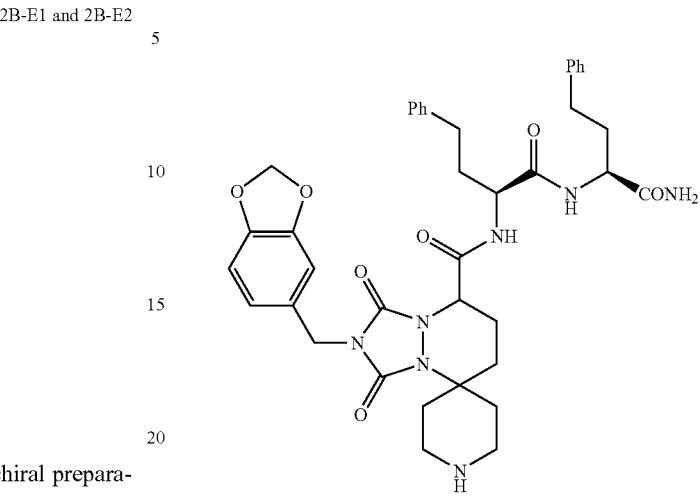

To a stirred solution of Example 2, Part 2A-E1 compound (80 mg, 0.2 mmol) in 2 mL of DMF were added PyAOP (115 mg, 0.22 mmol), TFA salt of Example 1, Part 1G compound (97 mg, 0.22 mmol) and DIEA (80 μL, 0.44 mmol) at RT, and the reaction was stirred at RT overnight. The reaction was diluted with EtOAc, washed with water (2×), dried over Na$_2$SO$_4$, filtered and concentrated. The intermediate was de-Boc with 1 mL of 30% TFA in dichloromethane (v/v) at RT for 2 h. It was concentrated and purified on prepLC. The purified product was then washed with NaHCO$_3$ to give 87 mg (60%) of the title compound (Example 2) as a white powder. LC=95% purity, Rt=3.07 min; LC-MS m/z=723 (M+H); $^1$H NMR (MeOH-d$_4$) δ 1.75-2.33 (m, 12H), 2.50-2.70 (m, 4H), 3.00-3.34 (m, 4H), 4.31-4.40 (m, 2H), 4.53 (d, J=6 Hz, 1H), 4.61 (d, J=6 Hz, 1H), 4.75 (t, J=6 Hz, 1H), 5.86 (d, J=6 Hz, 2H), 6.70 (d, J=9 Hz, 1H), 6.80-6.90 (m, 2H), 7.10-7.30 (m, 10H).

Example 3

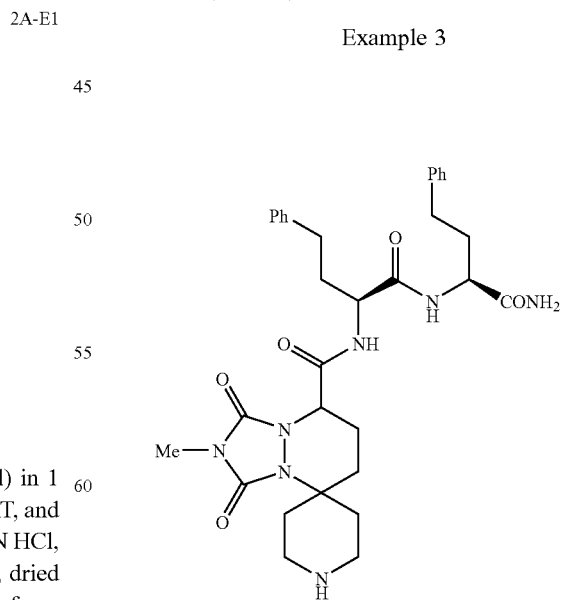

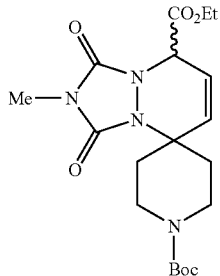

3A

Compound 3A was prepared from 4-methyltriazolidinedione and 1C according to the method of Example 1 (Part 1D) to give the title compound 3A (820 mg, 47%) as white solid. LC=97% purity; Rt=3.49 min. LC-MS m/z=431 (M+Na).

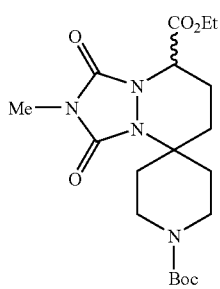

3B

Compound 3B was prepared from 3A according to the method described for Example 2 (Part 2A) to give the title compound 3B (820 mg, 100%) as white solid. LC=97% purity; Rt=3.37 min. LC-MS m/z=433 (M+Na).

3B-E1 and 3B-E2

Compound 3B (820 mg) was separated on a chiral preparative HPLC column packed with ChiralPak AS 2 μM (5×50 cm) using 10% absolute ethanol/90% hexanes as the solvents. The first eluting enantiomer was 3B-E1 (320 mg, 99% ee) and the second eluting enantiomer was 3B-E2 (370 mg, 78% ee).

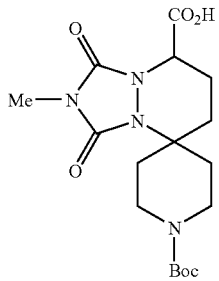

3C-E1

To a stirred solution of 3B-E1 (82 mg, 0.2 mmol) in a mixed solvent of methanol (1 mL) and THF (1 mL) was added 1N LiOH (0.8 mL, 0.8 mmol) at RT, and stirred at RT for 3 h. The solution was acidified with 1N HCl, then concentrated. It was extracted with EtOAc (3×), dried over $Na_2SO_4$, filtered and concentrated to give an oil 3C-E1 (80 mg, 100%).

Example 3

To a stirred solution of 3C-E1 (80 mg, 0.2 mmol) in 2 mL of DMF were added PyAOP (115 mg, 0.22 mmol), TFA salt of 1G (97 mg, 0.22 mmol) and DIEA (80 μL, 0.44 mmol) at RT, and the mixture was stirred at RT overnight. The reaction was diluted with EtOAc, washed with water (2×), dried over $Na_2SO_4$, filtered and concentrated. The intermediate was de-Boc with 1 mL of 30% TFA in dichloromethane (v/v) at RT for 2 h. It was concentrated and purified on prepLC to give 45.5 mg (32%) of the title compound (Example 3) as a TFA salt. LC=94% purity, Rt=2.46 min; LC-MS m/z=604 (M+H); $^1$H NMR (MeOH-$d_4$) δ 1.75-2.35 (m, 12H), 2.65-2.80 (m, 4H), 3.00 (s, 3H), 3.05-3.20 (m, 3H), 3.36 (t, J=6 Hz, 1H), 4.31-4.42 (m, 2H), 4.75 (t, J=6 Hz, 1H), 7.10-7.30 (m, 10H).

What is claimed is:

1. A compound of the structure

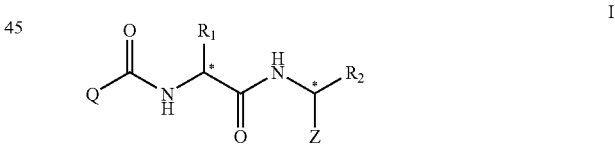

I or a pharmaceutically acceptable salt thereof, a prodrug ester thereof, and all stereoisomers thereof;

wherein $R_1$ and $R_2$ are the same or different and are independently selected from hydrogen, alkyl, aryl, cycloalkyl, alkenyl, alkynyl, arylalkyl, heteroaryl, heteroarylalkyl or heterocycloalkyl;

Z is selected from —$CON(R_4)R_{4a}$, —$CO_2R_4$, —$SO_2N(R_4)R_{4a}$, —$SO_2R_4$, CN, and

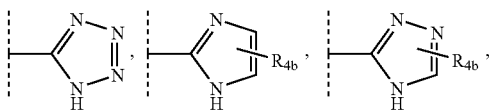

-continued

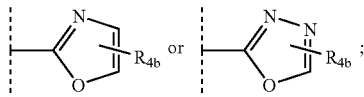

R₄ and R₄ₐ are the same or different and are independently selected from hydrogen, alkyl, cycloalkyl, aryl, arylalkyl, heteroaryl, or heteroarylalkyl, or R₄ and R₄ₐ can be joined together to form a heterocycle;

R₄ᵦ is selected from hydrogen, halogen, hydroxyl, CN, OCF₃, CF₃, CONH₂, SONH₂, SO₂CH₃, NHCOCH₃ or NHCO₂CH₃;

Q is a substituted bicyclic heterocycle selected from

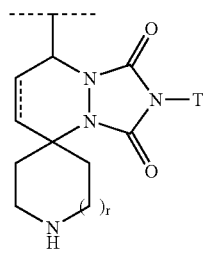

wherein r is 0, 1 or 2; and

represents a single bond or a double bond; and

T is selected from alkyl, aryl, cycloalkyl, alkenyl, alkynyl, arylalkyl, heteroaryl, heteroarylalkyl or heterocycloalkyl, and where each of these groups may be optionally substituted with R₅, R₅ₐ, and R₅ᵦ;

R₅, R₅ₐ and R₅ᵦ are the same or different and are independently selected from hydrogen, halogen, hydroxyl, OCF₃, CF₃, CN, NR₅꜀(R₅d), C(O)NR₅꜀(R₅d), OC(O)N (R₅꜀)R₅d, OR₅꜀, SO₂R₅꜀, SO₂N(R₅꜀)R₅d, alkyl, alkoxyl, aryl, arylalkyl, or heteroaryl; or R₅ and R₅ₐ can be joined together with —OCH₂O— or —OCH₂CH₂O— to form a fused bicyclic ring with aryl or a heteroaryl group;

R₅꜀ and R₅d are the same or different and are independently selected from hydrogen, alkyl, cycloalkyl, aryl, arylalkyl, heteroaryl, heteroarylalkyl, or heterocycloalkyl or R₅꜀ and R₅d can be joined together to form a heterocycle.

2. The compound as defined in claim 1 wherein Z is —CON(R₄)R₄ₐ.

3. The compound as defined in claim 1 wherein Z is CONH₂ and Q is

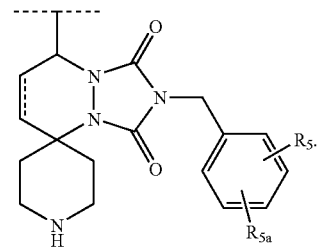

4. The compound as defined in claim 1 having the structure

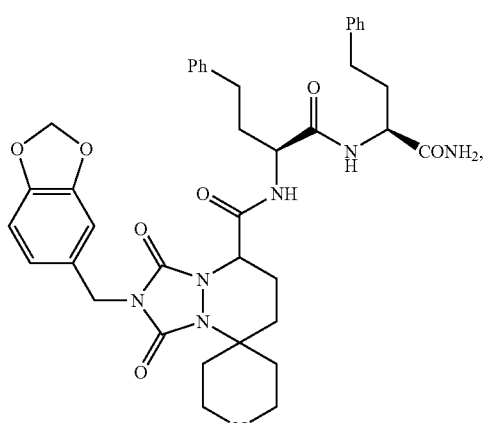

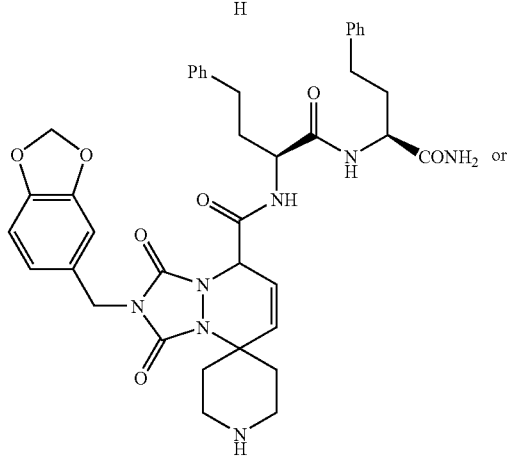

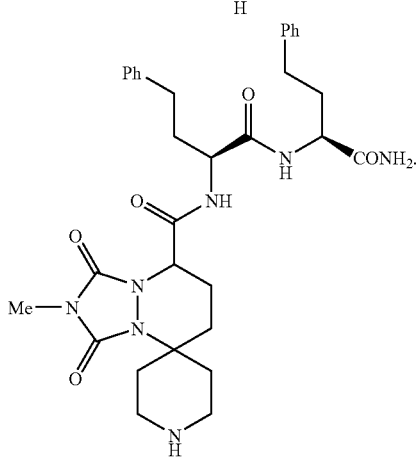

5. A pharmaceutical composition comprising a compound as defined in claim 1 and a pharmaceutically acceptable carrier therefor.

6. A pharmaceutical combination comprising a compound as defined in claim 1 and another therapeutically active compound.

7. The pharmaceutical combination as defined in claim 6 wherein the other therapeutically active compound is a proton pump inhibitor, a histamine H2 receptor blocker, an antacid, a gastrointestinal stimulant, a dopamine receptor blocker, a 5-HT4 agonist, a 5-HT3 antagonist, an anti-anorexia agent, an agent for gall bladder stasis, an agent for treating postoperative paralytic ileus, an agent for treating scleroderma, an agent for treating intestinal pseudo-obstruction, an anti-gastritis agent, an anti-emesis agent, an anti-constipation agent, an agent for treating irritable bowel syndrome, an agent for treating functional dyspepsia, or an agent for treating colonic hypomotility.

* * * * *